US010555707B2

(12) United States Patent
Cohen et al.

(10) Patent No.: US 10,555,707 B2
(45) Date of Patent: Feb. 11, 2020

(54) PATIENT SUPPORT SYSTEM AND METHOD FOR MEDICAL IMAGING

(71) Applicant: General Electric Company, Schenectady, NY (US)

(72) Inventors: Adam Israel Cohen, Milwaukee, WI (US); Douglas Grant, Muskego, WI (US); Joshua Lamb, Waukesha, WI (US); Johanna Sumner, Hartford, WI (US); Jiahua Fan, New Berlin, WI (US); Adam Pautsch, Oconomowoc, WI (US); John Moore Boudry, Waukesha, WI (US)

(73) Assignee: GENERAL ELECTRIC COMPAMNY, Schenectady, NY (US)

( * ) Notice: Subject to any disclaimer, the term of this patent is extended or adjusted under 35 U.S.C. 154(b) by 255 days.

(21) Appl. No.: 15/359,159

(22) Filed: Nov. 22, 2016

(65) Prior Publication Data
US 2018/0140261 A1 May 24, 2018

(51) Int. Cl.
*A61B 6/04* (2006.01)
*A61G 7/10* (2006.01)

(52) U.S. Cl.
CPC .......... *A61B 6/0464* (2013.01); *A61G 7/1001* (2013.01); *A61G 7/1042* (2013.01)

(58) Field of Classification Search
CPC .................................... A61B 6/04
USPC .......................................... 5/601
See application file for complete search history.

(56) References Cited

U.S. PATENT DOCUMENTS

| | | |
|---|---|---|
| 3,897,345 A | 7/1975 | Foster |
| 4,145,612 A | 3/1979 | Cooper |
| 4,146,793 A | 3/1979 | Bergstrom |
| 4,262,204 A | 4/1981 | Mirabella |
| 4,914,682 A | 4/1990 | Blumenthal |
| 4,926,457 A | 5/1990 | Poehner et al. |
| 4,939,801 A * | 7/1990 | Schaal ................... A61G 7/001 5/607 |
| 4,956,885 A | 9/1990 | Alich et al. |
| 5,054,049 A | 10/1991 | Manabe et al. |
| 5,225,980 A | 7/1993 | Hiseh et al. |
| 6,446,286 B1 | 9/2002 | Karmalawy |
| 7,638,775 B2 | 12/2009 | Kogan et al. |
| 8,276,225 B2 | 10/2012 | Kogan et al. |
| 8,594,273 B2 | 11/2013 | Ishii |
| 2005/0059877 A1 | 3/2005 | Falbo |
| 2012/0170710 A1* | 7/2012 | Niedzielski .......... A61B 6/0442 378/20 |

\* cited by examiner

*Primary Examiner* — Fredrick C Conley
(74) *Attorney, Agent, or Firm* — Fletcher Yoder, P.C.

(57) ABSTRACT

A patient support system includes a support beam that may translocate along an axial axis of a medical imaging system. At least a portion of the support beam may be disposed within a central bore of the medical imaging system. The patient support system also includes a patient support removably coupled to the support beam and including a backing that may support a patient during an imaging procedure and a restraint extending a longitudinal length of the backing. The restraint includes a first end coupled to the backing and a second end that may be removably coupled to the support beam, and the restraint may secure the patient support to the support beam and to restrain the patient within the patient support.

18 Claims, 5 Drawing Sheets

PATIENT SUPPORT SYSTEM AND METHOD FOR MEDICAL IMAGING

BACKGROUND

The subject matter disclosed herein relates to medical imaging and, in particular, to a patient support system for transferring and supporting a patient for medical imaging.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the emission of gamma radiation, to acquire data and to construct images or otherwise represent the observed internal features of the patient.

Traditionally, medical imaging systems, such as a computed tomography (CT) imaging system or a CT/positron emission tomography (PET) imaging system, include a gantry and a patient table. The patient table needs to be as transparent as possible to X-rays used by the CT imaging system and the gamma rays used by the PET imaging system. As a result, the tables are constructed of thin, composite materials which need to support several hundred pounds of weight. The patient table includes a cantilevered patient support (e.g., cradle or pallet) that extends from the table into the gantry bore. However, patient supports having a cantilevered configuration generally have a vertical thickness that may attenuate the radiation (e.g., X-rays and gamma radiation) and induce undesirable noise during medical imaging procedures. For example, the vertical thickness of the cantilevered patient support may have a large amount of material to fill a large cross-sectional area such that the cantilevered patient support has sufficient strength to support patients of various size and weight. As such, radiation dose efficiency and image quality may be affected by the vertical thickness of the cantilevered patient table.

BRIEF DESCRIPTION

In one embodiment, a patient support system includes a support beam that may translocate along an axial axis of a medical imaging system. At least a portion of the support beam may be disposed within a central bore of the medical imaging system. The patient support system also includes a patient support removably coupled to the support beam and including a backing that may support a patient during an imaging procedure and a restraint extending a longitudinal length of the backing. The restraint includes a first end coupled to the backing and a second end that may be removably coupled to the support beam, and the restraint may secure the patient support to the support beam and to restrain the patient within the patient support.

In a second embodiment, a medical imaging system includes a patient support system having a support beam that may translocate along an axial axis of the medical imaging system. At least a portion of the support beam may be disposed within a central bore of the medical imaging system. The medical imaging system also includes a patient support removably coupled to the support beam and having a backing that may support a patient during an imaging procedure and a restraint extending a longitudinal length of the backing. The restraint includes a first end coupled to the backing and a second end that may be removably coupled to the support beam, and the restraint may secure the patient support to the support beam and to restrain the patient within the patient support.

In a third embodiment, a method includes coupling a patient support having a patient to a support beam of a patient support system of a medical imaging system. The patient support includes a backing that may support a patient during an imaging procedure and a restraint extending a longitudinal length of the backing, the restraint includes a first end coupled to the backing and a second end that may removably couple the patient support to the support beam such that the restraint is oriented orthogonal to the backing, and the restraint may secure the patient support to the support beam and to restrain the patient within the patient support. The method also includes moving the support beam in a first direction to position the patient support within a central bore of the medical imaging system using a translocation system coupled to the support beam.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As described herein, in certain instances medical imaging systems, such as a computed tomography (CT) imaging system or a CT/positron emission tomography (PET) imaging system, include a patient table that includes a cantilevered patient support (e.g., cradle or pallet) that extends from the table into a gantry bore. However, a configuration of the cantilevered patient support may attenuate radiation (e.g., X-ray and gamma radiation) used to image a patient. For example; the cantilevered patient support may have a large vertical thickness (e.g., cross-sectional area) such that the cantilevered patient support has sufficient material density to provide a strength suitable to support patients of various size and weight. The material density of the cantilevered patient support may attenuate the radiation (e.g., by absorbing and/or scattering the radiation) and increase noise levels during medical imaging. Accordingly, radiation dose efficiency may be decreased and an amount of radiation used during medical imaging may need to be increased to account for the attenuated radiation such that the patient receives a radiation dose suitable for producing a desired image quality.

Additionally, in certain medical settings, the patient may need to be transported from a patient bed to the cantilevered patient support of the medical imaging system. Transferring patients to and from the cantilevered patient support (e.g., patient table) may be difficult depending on the patient's size, weight, and medical status. During certain medical imaging procedures, medical staff transport the patient to and from the patient support to the patient bed, which may result in patient and/or medical staff discomfort. For example, depending on the patient's size, weight, and/or medical status (e.g., critical, stable, etc.), it may be difficult to safely move the patient from a patient bed or wheelchair onto the cantilevered support. Accordingly, it may be desirable to use a patient support that may be easily positioned underneath the patient while the patient is on the patient bed or gurney (e.g., if the patient arrives in an ambulance to a clinic or hospital setting), and improves radiation dose efficiency and noise levels. Disclosed herein is a non-cantilever patient support system having a hammock-like configuration that may facilitate patient transfer to and from the medical imaging system and may also reduce attenuation of the radiation and noise levels during medical images compared to cantilevered patient support systems.

Figure 1:
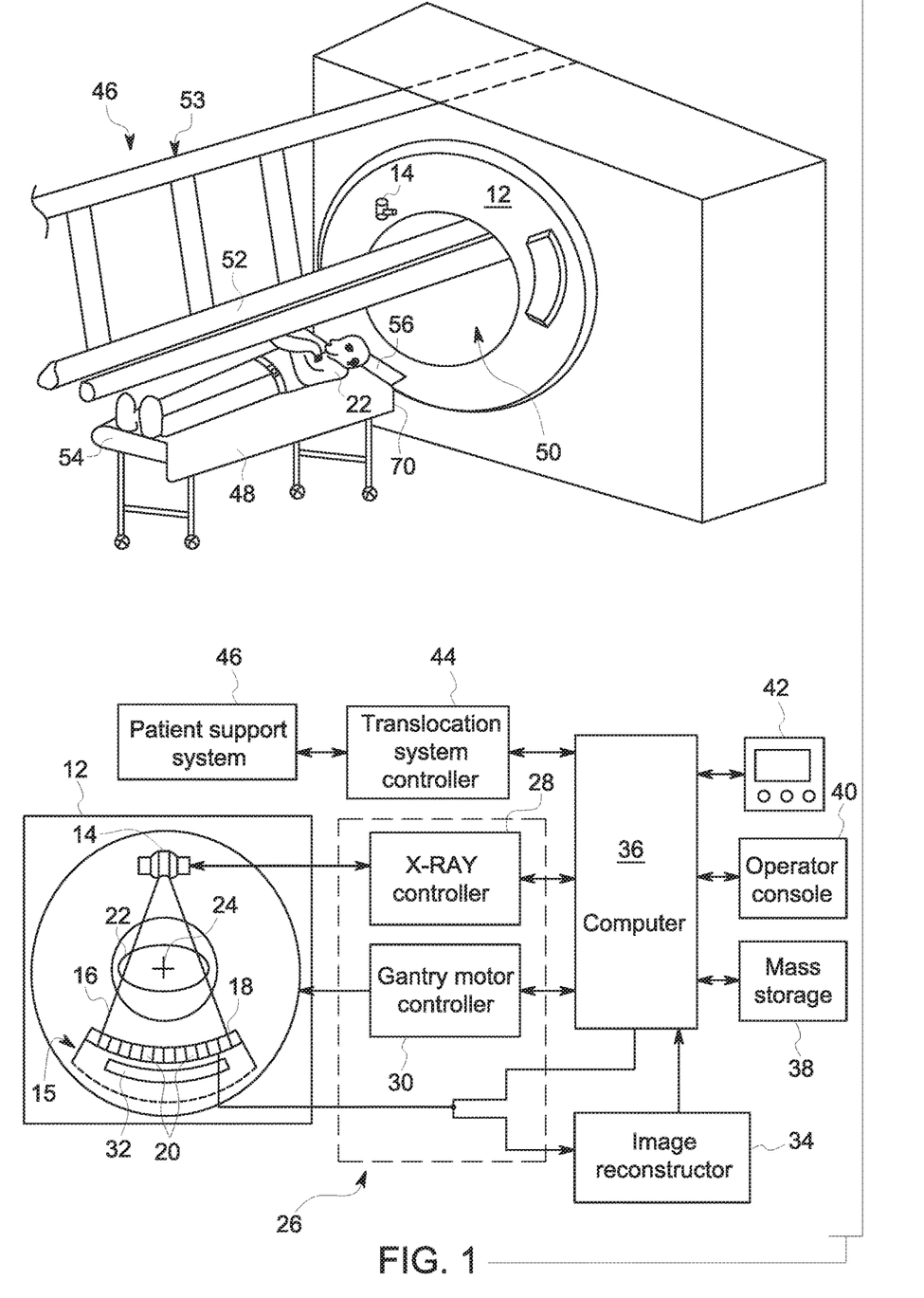
FIG. 1 is a combined pictorial view and block diagram of a computed tomography (CT) imaging system having a removable patient support, in accordance with an embodiment of the present disclosure.

Although the following embodiments are discussed in terms of a computed tomography (CT) imaging system, the embodiments may also be utilized with other imaging systems (e.g., PET, CT/PET, SPECT, nuclear CT, etc.). With the foregoing in mind FIG. 1 is a diagram of a CT imaging system 10 that may be used for medical imaging procedures. The CT imaging system 10 includes a gantry 12. The gantry 12 has an X-ray source 14 that projects a beam of X-rays 16 toward a detector assembly 15 on the opposite side of the gantry 12. The detector assembly 15 includes a collimator assembly 18, a plurality of detector modules 20, and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to the X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a translocation system controller 44, which controls movement of a patient support system 46 that supports the patient 22 during an imaging procedure. Particularly, the translocation system controller 44 moves the patient support system 46 into and through a gantry opening or bore 50 to position the patient 22 within the medical imaging system 10. The patient support system 46 includes a patient support 48 that retains and secures the patient 22 during the imaging procedure. As described in greater detail below, the patient support system 46 may include support beams 52 and a translocation system 53 that secure and linearly move the patient support 48 during the imaging procedure.

The patient support 48 may be removably attached to the support beams 52 to facilitate loading and unloading of the patient 22. For example, the patient support 48 may be positioned on a patient bed 54 that may be used to transport the patient 22 to the medical imaging system 10. In certain medical settings (e.g., a clinic or hospital), the patient may be assigned to a room that is separate from where the medical imaging system 10 is located. The patient support 48 may be placed on a patient surface 56 of the patient bed 54 and underneath the patient 22 before or after transporting the patient 22 to the medical imaging system 10. As discussed in further detail below, the patient support 48 may include a restraint one or more attachment features that secure the patient 22 and the patient support 48 to the support beams 52, respectively, during the medical imaging procedure. Once the patient 22 and the patient support 48 are properly secured, a height of the bed 54 may be adjusted to lower and/or remove the bed 54 from underneath the patient support 48. Accordingly, the patient 22 may be suspended in the patient support 48 (e.g., similar to a hammock) before moving the patient 22 into the bore 50 for the imaging procedure.

Figure 2:
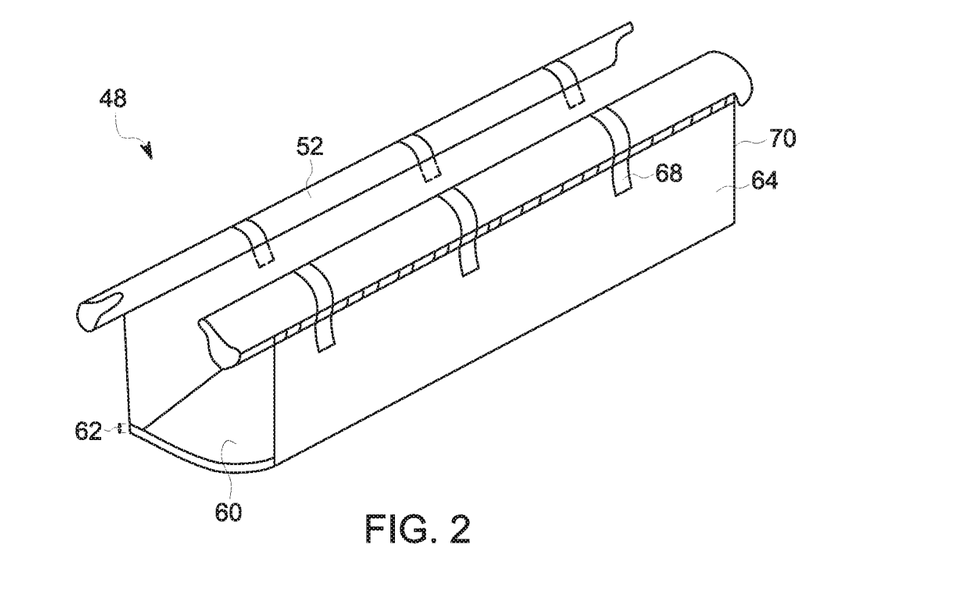
FIG. 2 is perspective view of a patient support system having a hammock-like configuration that may be used with the CT imaging system of FIG. 1, whereby the patient support system restrains a patient during an imaging procedure, in accordance with an embodiment of the present disclosure.

As discussed above, patient tables used in certain medical imaging systems may attenuate radiation and cause undesirable noise, which may affect radiation dose efficiency and image quality. The patient support system 46 disclosed herein includes features that may mitigate the undesirable effects of patient tables used in certain medical imaging systems. In addition, the patient support 48 of the patient support system 46 may be removable, which may facilitate patient loading and unloading before and after, respectively, the imaging procedure. FIG. 2 illustrates a perspective view of the patient support system 46 that may be used to support the patient 22 during medical imaging. In the illustrated embodiment, the patient support 48 includes a backing 60 that abuts against the patient 22 when the patient 22 is loaded onto the patient support 48 and provides support for the patient 22 during the imaging procedure. The backing may be rigid for structural support. By way of non-limiting example, the backing 60 may be manufactured from durable materials such as carbon fiber, fiber glass, composite materials, resins, or any other suitable material is transparent to radiation (e.g., X-rays and/or gamma rays), and combinations thereof. In certain embodiments, the backing 60 may have a contoured surface that may outline a body shape for patient comfort.

To mitigate attenuation of radiation (e.g., the beam of X-rays 16), the backing 60 may have a cross-sectional area that is between approximately 50% to 95% less than a cross-sectional area of the patient table used in cantilevered patient support systems associated with certain medical imaging systems. As such, the backing 60 uses less material than the patient table in cantilevered patient support systems. For example, in a non-cantilevered configuration, a first vertical dimension 62 (e.g., thickness/cross-sectional area) of the backing 60 and a second vertical dimension 63 (e.g., thickness/cross-sectional area) of the support beams 52 are such that a total cross-sectional area of the backing 60 and the support beams 52 is between approximately 50% and 95% less than a vertical dimension of the patient table used in cantilevered patient support systems. Due, in part, to the use of less material for the backing 60, the patient support system 46 may minimize attenuation and scattering of the beam of X-rays 16 during imaging of the patient 22. In certain embodiments, the patient support system 46 may attenuate between approximately 0% and 10% of the beam of X-rays 16 during the imaging procedure. As such, radiation dosing efficiency and image quality may be improved during the imaging procedures.

Figure 3:
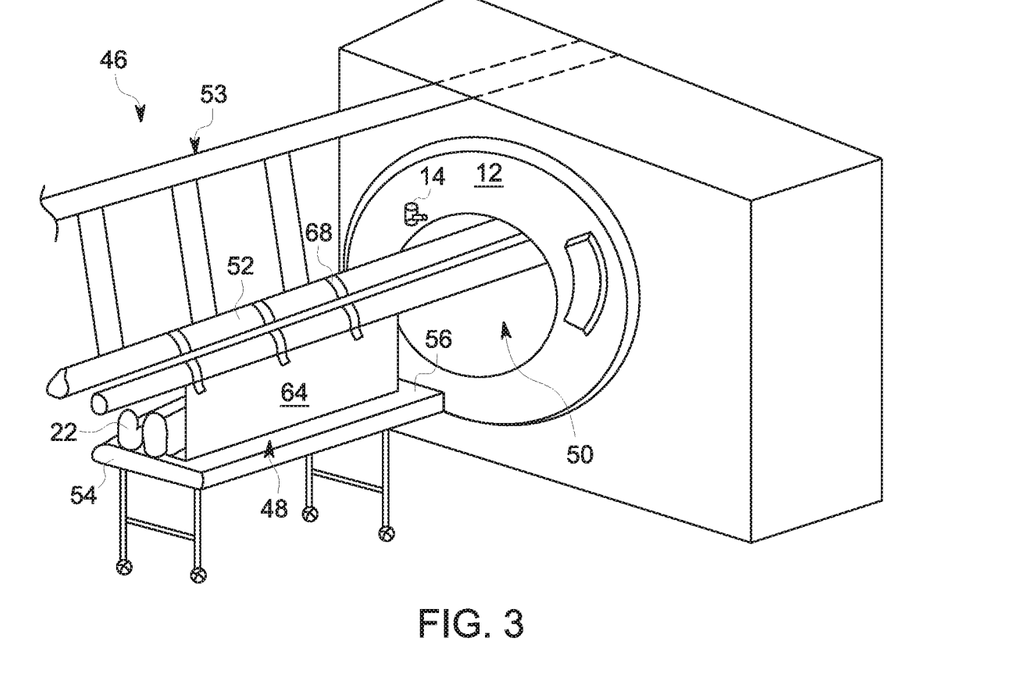
FIG. 3 is a pictorial view of the CT imaging system of FIG. 1, whereby the patient is restrained within the patient support system of FIG. 2, in accordance with an embodiment of the present disclosure.

In addition to the backing 60, the patient support 48 includes a restraint 64 attached to the backing 60. The restraint 64 may be used to secure the patient 22 within the patient support 48 during the imaging procedure, and may facilitate removably coupling the patient support 48 to the support beams 52. For example, as illustrated in FIG. 2, the patient support 48 may have a hammock-like configuration such that when the patient 22 is secured within the patient support 48 and no longer supported by the patient bed 54, the patient 22 is suspended by the patient support system 46, as shown in FIG. 3. Therefore, the patient 22 may be cradled within the patient support system 46 when the restraint 64 is coupled to the support beams 52. The restraint 64 may include materials that are flexible, breathable, and provide patient comfort. Moreover, the restraint 64 may include materials that have a suitable tensile strength to support patients of various size and weight, low X-ray attenuation (e.g., attenuate less than approximately 10% of the beam of X-rays 16 or other suitable medical imaging radiation), and be readily cleaned (e.g., wiped, laundered, sterilized) for reuse. By way of non-limiting example, the restraint 64 may include a fabric such as nylon, cotton, canvas, polyester, or any other suitable heavy duty fabric. In certain embodiments, the backing 60 and the restraint 64 may be coated with an anti-microbial material to maintain sterility.

As discussed above, the restraint 64 may be coupled to the support beams 52 to secure and suspend the patient 22 during the imaging procedure. Accordingly, the patient support 48 may include attachment features that secure the restraint 64 to the support beams 52. For example, the restraint 64 may include a plurality of fasteners 68 that may be removably attached to the support beams 52 to secure restraint to the support beams 52. For example, during the imaging procedure, medical staff may raise and restraint end 70 above the patient 22 and toward a corresponding support beam 52 to attach the restraint 64 to the support beam 52 using the plurality of fasteners 68.

The plurality of fasteners 68 may include any suitable fastener that secures the restraint 64 to the support beams 52 and has a suitable tensile strength such that the patient 22 may be safely suspended and transported into and out of the bore 50 of the medical imaging system 10. In one embodiment, the plurality of fasteners 68 may include a Velcro® belt or any other suitable belt that may wrap around at least a portion of the support beams 52 to secure the restraint 64 to the support beams 52. In another embodiment, the plurality of fasteners 68 may include hooks that may be hooked onto the support beams 52 or may be inserted into complementary openings on the support beams 52 to secure the restraint 64 to the support beams 52. In certain embodiments, the plurality of fasteners 68 may be coupled to complementary fasteners on the support beams 52 (e.g., a snap fit connection) to secure the restraint 64 to the support beams 52. In other embodiments, the plurality of fasteners 68 may include a combination of different fasteners (e.g., belts, hooks, snap-fit fasteners, etc.) to secure the restraint 64 to the support beams 52.

The hammock-like configuration of the patient support system 46 enables the use of less materials for the backing 60, while still maintaining a suitable structural integrity and strength to support patients of various size and weight. In certain embodiments, the support beams 52 and/or translocation system 53 of the patient support system 46 may be designed as structural beams having a higher moment of inertia compared to a patient table in a cantilevered patient support system. Accordingly, the patient support system 46 may provide a strength to weight ratio that allows for less material to be used in the patient support 48 compared to the patient table in the cantilevered patient support system. By configuring the support beams 52 and the translocation system 53 to be support structures for the patient support system 46, the structural components of the patient support system 46 may be kept away from a scan region of interest of the medical imaging system 10.

Additionally, by using less material for the backing 60, a cross-sectional area of the backing 60 and support beams 52 may be decreased compared to the patient table in cantilevered patient support systems. Accordingly, less radiation may be attenuated and scattered, which may result in an increase in radiation dose efficiency and noise levels compared to cantilevered patient support systems used in certain medical imaging systems. For example, noise levels generally associated with cantilever patient support systems may be decreased by approximately 50% to 85%. This is due, in part, to the decreased cross-sectional area (e.g., vertical dimension 62) of the backing 60 compared to the patient table of cantilevered patient support systems. For example, the reduced cross-sectional area of the backing 60 may scatter less radiation compared to the patient table used in cantilevered patient support systems. As such, the disclosed patient support 48 may increase radiation dose efficiency and provide a suitable image quality using less radiation compared to cantilevered patient support systems used in certain medical imaging systems.

Moreover, a rotational speed of the medical imaging system 10 may be increased compared to medical imaging systems that use a cantilevered patient support system, which may enable a decrease in the radiation dose. Additionally, the patient support 48 may enable utilizing faster rotational speeds during the imaging procedure, which may increase the image quality, in particular for patients having a large body mass index (BMI). Therefore, an amount of time that may be needed for imaging the patient 22 and generate images having a desirable image quality may be decreased, which may also increase patient turnaround (e.g., workflow) compared to cantilevered patient support systems.

Furthermore, the hammock-like configuration of the patient support 48 may allow flexibility with patient positioning. For example, the restraint 64 may block the patient 22 from rolling off the backing 60. Therefore, the patient 22 may be positioned on their side (e.g., lateral position) or may be tilted with minimal patient movement. The restraint 64 may contain the patient 22 in the tilted position, while also restraining the patient 22 within the patient support 48. The patient support 48 may also provide a certain degree of comfort for the patient 22 due to the hammock-style configuration of the patient support 48.

Figure 4:
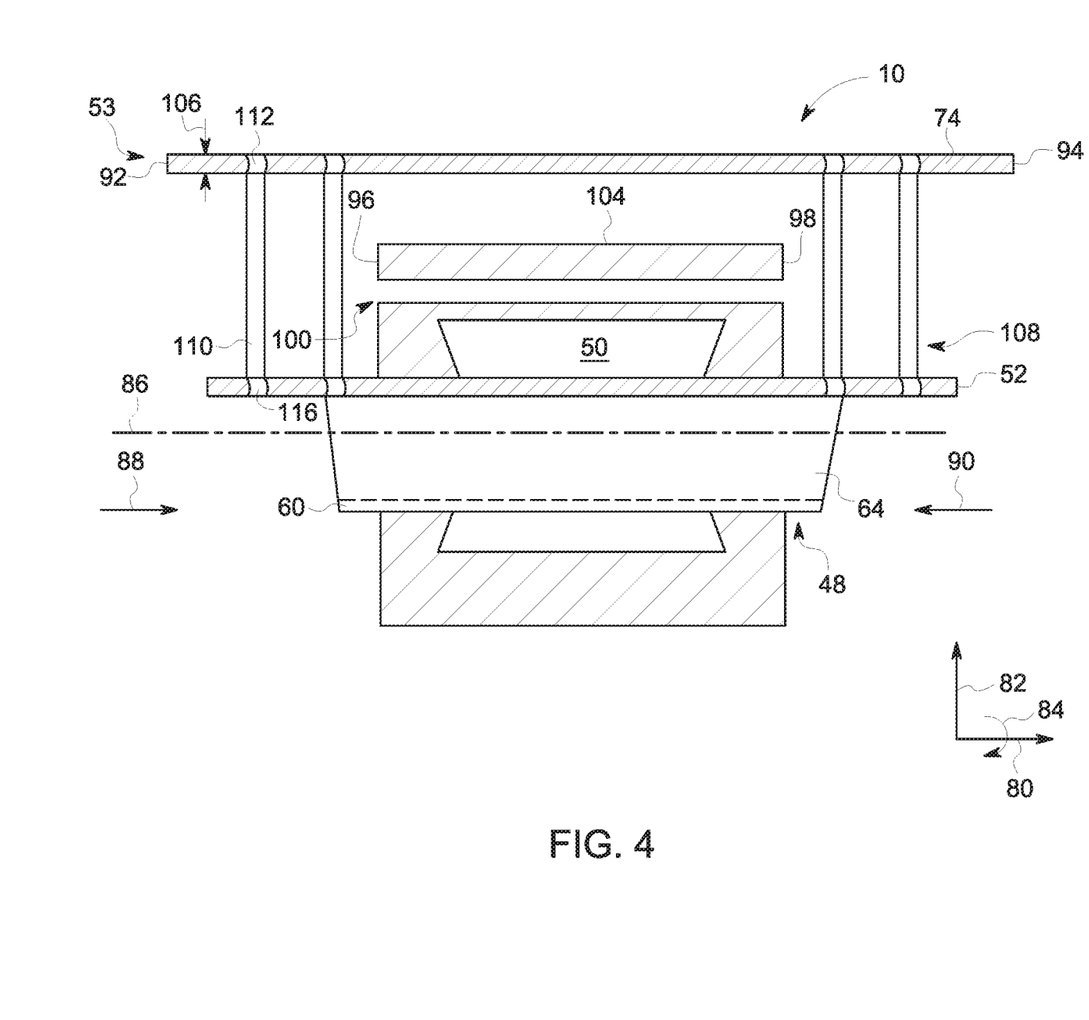
FIG. 4 is a cross-sectional view of the CT imaging system of FIG. 1, whereby a linear translocation system coupled to the CT imaging system is used to move the patient support system of FIG. 2, in accordance with an embodiment of the present disclosure.

As discussed above, the patient support 48 may be used to support the patient 22 during medical imaging procedures. The patient support 48 may be removably attached (e.g. secured) onto the support beams 52, which may be coupled to the translocation system 53 that moves (e.g., mechanically or pneumatically) the support beams 52 during medical imaging. FIG. 4 is a cross-sectional view of the medical imaging system 10 in which the translocation system 53 includes one or more tracks 74 that linearly translocate the patient support system 48 into and out of the bore 50 during the imaging procedure. The medical imaging system 10 may have an axial axis or direction 80, a radial axis or direction 82 away from axis 80, and a circumferential axis or direction 84 around axis 80. For example, the axis 80 corresponds to a longitudinal centerline 86 or lengthwise direction, the axis 82 corresponds to a crosswise or radial direction relative to the longitudinal centerline 86, and the axis 84 corresponds to the circumferential direction about the longitudinal centerline 86. The one or more tracks 74 may guide and direct the patient support system 46 (e.g., the support beams 52) along the axis 80 (e.g., the centerline axis 86) in a first direction 88 such that the patient 22 is properly aligned within the bore 50 for imaging. Similarly, the one or more tracks 74 may guide and direct the patient support 48 (e.g., the support beams 52) along the axis 80 in a second direction 90 that is substantially opposite the first direction 88 such that the patient 22 is properly aligned with the patient bed 54 after the imaging procedure to load the patient 22 on the patient bed 54 and unload the patient support system 46. The one or more tracks 74 may extend along the longitudinal axis 86 of the medical imaging system 10 such that ends 92, 94 of the one or more tracks 74 extend an axial distance 95 away from lateral end faces 96, 98 of the medical imaging system 10.

In certain embodiments, the support beams 52 may be fixedly attached to the one or more tracks 74. In other embodiments, the support beam 52 may be removably coupled to the one or more tracks 74 such that the support beams 52 may be removed from within gantry 12. By removing the support beams 52 from the gantry, the support beams 52 may not interfere with calibration of the medical imaging system 10 and scattering of radiation (e.g., the beam of X-rays 16) emitted during the imaging procedure.

It may be desirable to position the one or more tracks 74 away from the bore 50 to avoid the one or more tracks 74 interfering with the medical imaging system 10 and scattering of radiation (e.g., the beam of X-rays 16) emitted during the imaging procedure. For example, in the illustrated embodiment, at least a portion of the one or more tracks 74 is disposed within a passage 100 positioned between a top end face 104 of the medical imaging system 10 and the bore 50. The passage 100 extends along the longitudinal axis 86 of the medical imaging system 10 and is sized to accommodate an outer dimension 106 of the one or more tracks 74. That is, the passage 100 may have an inner dimension that is substantially equal to or greater than the outer dimension 106. In this particular embodiment, at least a portion of the one or more tracks 74 is coupled to the medical imaging system 10 such that the medical imaging system 10 provides structural support for the one or more tracks 74. By positioning at least a portion of the one or more tracks 74 within the passage 100, may not interfere with calibration and imaging processes during use of the medical imaging system 10.

In one embodiment, the ends 92, 94 may be secured to a wall of a room where the medical imaging system 10 may be located or any other suitable structure (e.g., the room ceiling or floor) within the imaging room. In certain embodiments, the ends 92, 94 may not be attached to any structure (e.g., the wall of the imaging room). In other embodiments, the support beams 52 may include to end that are substantially opposite the ends 92, 94. The ends opposite the ends 92, 94 may be secured onto a top a lateral face 96, 98 and near the top end face 104 of the system 10. The translocating system 53 may include cabling or any other suitable retaining feature (e.g., a beam) that extends from the ceiling and or walls of the imaging room. The cabling may couple to portions of the one or more tracks 74 to hold the one or more tracks in tension and secure the portions of the one or more tracks 74 to fixed structures (e.g., the ceiling and/or wall) of the imaging room and provide additional structural support for the one or more tracks 74.

In certain embodiments, the one or more tracks 74 may not be coupled to the medical imaging system 10. Rather the one or more tracks 74 may be separate from the medical imaging system 10. For example, the one or more tracks 74 may be suspended from the ceiling and/or walls of the room where the medical imaging system 10 is located. The one or more tracks 74 may be attached to cables and/or beams using bolts, screws, fasteners, or any other suitable retaining feature to suspend and secure the one or more tracks 74. The cables and/or beams are configured to provide structural support and strength such that the translocation system 53 may sustain loads associated with the various sizes and weights of the patient 22 being imaged.

The translocation system 53 may include movable coupling system that may attach to the one or more tracks 74 and the support beams 52. For example, in the illustrated embodiment, the translocation system 53 includes a movable coupling system 108 having a plurality of extensions 110 that radially 82 extend between each track of the one or more tracks 74 and the support beam 52. The plurality of extensions 110 may couple the one or more tracks 74 to the support beams 52, and facilitate linear movement of the patient support system 48 into and out of the bore 50 of the medical imaging system 10. For example, the plurality of extensions 110 may couple portions of the support beams 52 that extend away from the bore 50 of the medical imaging system 10 to the one or more tracks 74. In this way, the translocation system 53 may remain external to the bore 50 and may not interfere with the radiation emitted (e.g., the beam of X-rays 16) during imagining and/or calibration of the medical imaging system 10.

The plurality of extensions 110 include a first end 112 that couples to the one or more tracks 74 and a second end 116 that couples to the support beams 52. The first end 112 may include a hook or ring that couples to a moveable feature (e.g., a moving rack, chain, conveyer belt, beam, or other suitable moving feature) disposed on the one or more tracks 74. The translocation system controller 44 may control movement of the plurality of extensions 110 to enable the patient support 48 to translocate into and out of the bore 50. For example, a user of the medical imaging system 10 may instruct the translocation system controller 44 to move the patient support 48 into and out of the bore 50 of the medical imaging system 10. For example, the translocation system controller 44 may control movement of the movable feature of the one or more tracks 74 and, consequently, the plurality of extensions 110 and the patient support 48 may move into or out of the bore 50. The second end 116 may be fixed on the support beams 52 to allow movement of the patient support 48 into and out of the bore 50 when the first end 112 moves relative to the one or more tracks 74. In this way, the translocating system 53 may move the patient 22 into and out of the bore 50 for medical imaging, as shown in FIGS. 3 and 4.

In certain embodiments, the first end 112 may not move relative to the one or more tracks 74. Rather, the second end 116 may include features that may grasp and move the support beams 52 into and out of the bore 50. For example, each extension of the plurality of extensions 110 may include a robotic arm. The second end 116 of each extension of the plurality of extensions 110 may be a robotic hand that may grasp and pull the support beams 52 in the direction 88, 90 to move the patient support 48 into and out of the bore 50. In other embodiments, the second end 116 may include a rotating wheel that when rotated in the second direction 90 moves the support beams 52 in the first direction 88 to move the patient support 48 and the patient 22 into the bore 50. The rotating wheel may also rotate in the first direction 88 to move the patient support 48 in the second direction 90 such that the patient support 48 and the patient 22 may be moved out of the bore 50.

By suspending the patient support 48 from the translocating system 53 and linearly moving the patient support 48 into and out of the bore 50 using the translocating system 53, the patient 22 may be positioned within the bore 50 in a less amount of time compared to cantilevered patient support systems, and patient workflow may be increased. Additionally, the hammock-like configuration of the patient support system 46 disclosed herein may enable the cross-sectional area of the backing 60 to be decreased compared to the patient table used in cantilevered patient support systems, which may increase radiation dose efficiency during imaging by decreasing attenuation and scattering of the radiation (e.g., the beam of X-rays 16) and noise levels. As such, the rotational speed of the gantry 22 may be increased, in particular for patient's having a large body mass index (BMI). Moreover, the patient support 48 may allow flexibility for patient positioning. For example, the patient support 48 may facilitate placing the patient in a tilted or lateral positon safely and mitigate patient movement due, in part, to the restraint 64 of the patient support 48. Furthermore, the hammock-like configuration of the patient support 48 may increase patient comfort compared to the patient table of cantilevered patient support systems that may be used in certain medical imaging systems.

Figure 5:
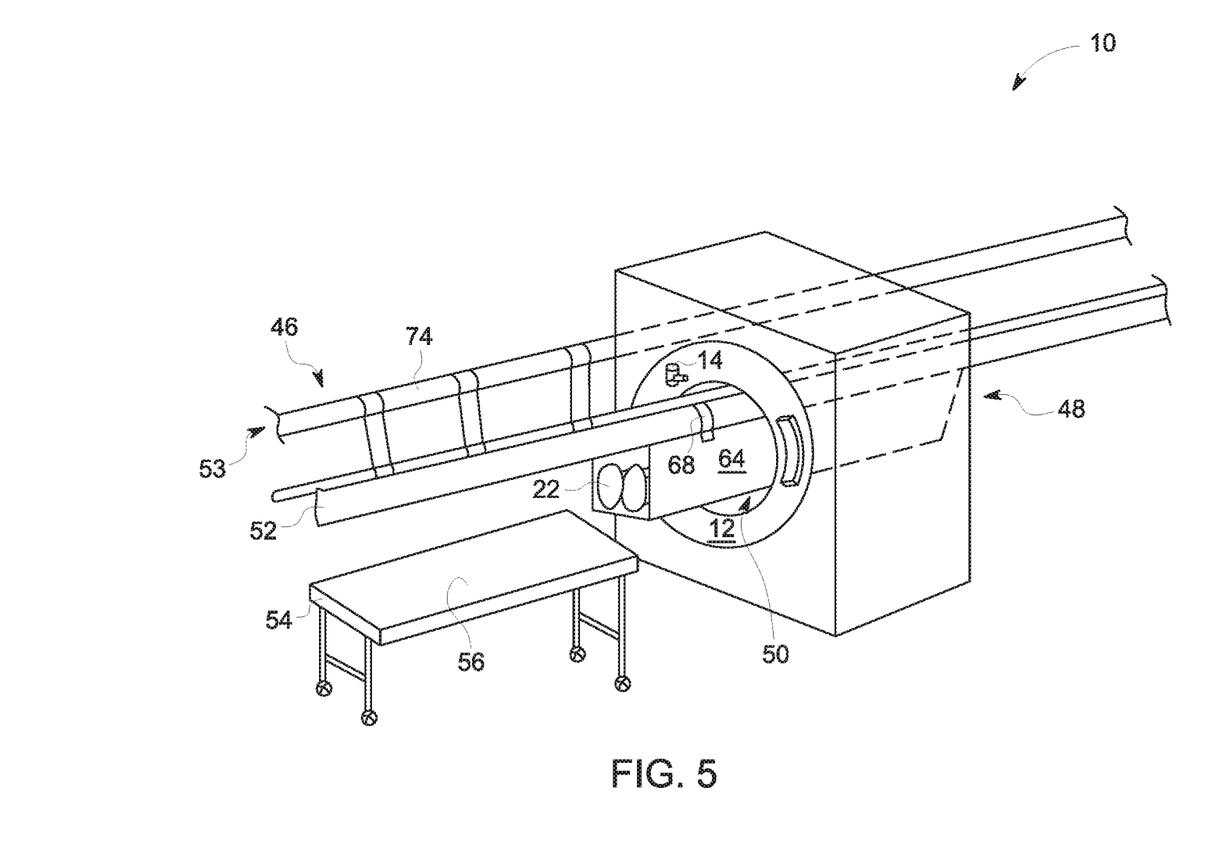
FIG. 5 is a pictorial view of the CT imaging system of FIG. 1, whereby the patient is positioned within a bore of the CT imaging system during an imaging procedure using the patient support system of FIG. 2, in accordance with an embodiment of the present disclosure.
Figure 6:
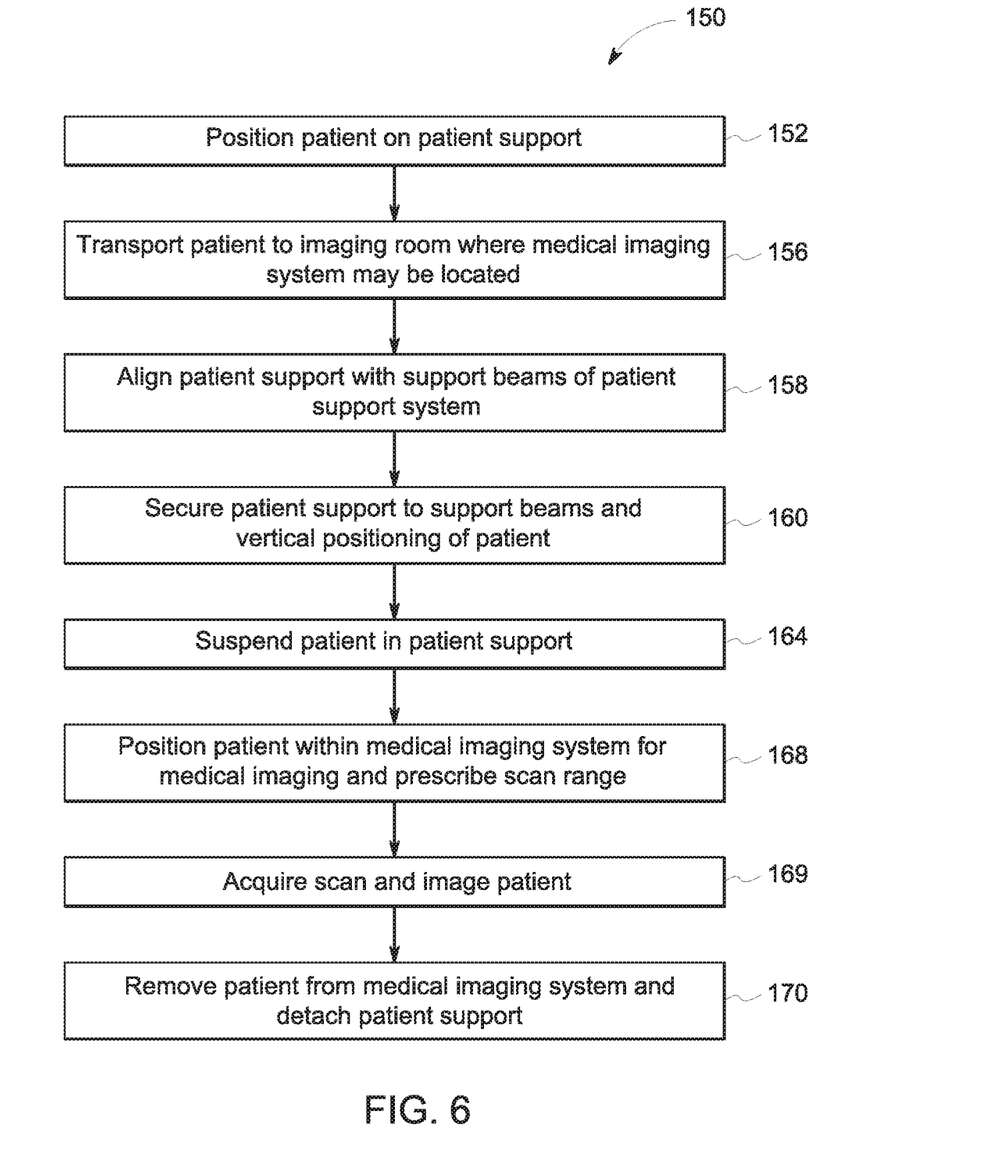
FIG. 6 is a flow diagram of a method for transporting and positioning a patient within the CT imaging system using the patient support of FIG. 2, in accordance with an embodiment of the present disclosure.

Present embodiments of the disclosure also include a method of using the patient support system for loading and unloading the patient 22 onto the patient support system 46, and positioning the patient 22 within the medical imaging system 10 for medical imaging. FIG. 6 is an embodiment of a method 150 that may be used to transport and position the patient 22 within the medical imaging system 10. To facilitate discussion of aspects of the method 150, reference is made to corresponding diagrams resulting from the acts of the method 150 in FIGS. 1, 3, and 5.

The method 150 includes positioning (e.g., loading) the patient 22 on the patient support 48 (block 152). Before transporting the patient to the imaging room where the medical imaging system 10 may be located, a portion of the patient support 48 (e.g., the backing 60 and the restraint 64) may be placed on patient surface 56 of the patient bed 54. For example, in certain embodiments, the patient 22 may be rolled onto their lateral side such that the backing may be placed against the back of the patient 22. The patient 22 may then be rolled onto their back such that the backing 60 lays flat on the patient surface 56 of the patient bed 54. The ends 70 of the restraint 64 may be draped over edges of the patient bed 54 similar to a sheet over the patient bed 54, as seen in FIG. 1. Rolling the patient 22 onto their lateral side may facilitate positioning of the patient 22 on the patient support 48 in medical situations where the patient 22 is unable to move away from the patient bed 54 (e.g., due, in part, to patient status, limited medical staff to assist in patient positioning, etc.). Additionally, in medical situations where the patient 22 arrives to a clinic or hospital setting on an ambulance, the patient 22 may be on an ambulance board and/or gurney. The patient 22 may be easily positioned on the patient support 48 by rolling the patient onto their lateral side and sliding (e.g., positioning) the backing 60 against the patient's back or the patient surface 56 of the patient bed 54. The patient support 48 may be used to transfer the patient 22 to a hospital bed (e.g., the patient bed 22) from the ambulance board and/or gurney.

In other embodiments, the patient 22 may be able to get out of the patient bed 54 such that the medical staff may place the patient support 48 on the patient bed 54. In this particular embodiment, the backing 60 may be positioned directly onto the patient surface 56 of the patient bed 54 such that a longitudinal length of the backing 60 abuts the patient surface 56 of the patient bed 54. Once the patient support 48 is correctly positioned on the patient bed 54, the patient 22 may return to the patient bed 54 and lay over the backing 60 of the patient support 48 (see, e.g., FIG. 1).

Following positioning of the patient 22 on the patient support 48, the method 150 includes transporting the patient 22 to the imaging room where the medical imaging system 10 may be located (block 156). As discussed above, the patient 22 may be positioned on the patient support 48, which is supported by the patient bed 54, at a remote location (e.g., patient room, emergency room, or other area away from the medical imaging system 10). Once on the patient support 48, the patient 22 may be wheeled into the imaging room using the patient bed 54.

The method 150 also includes aligning the patient support 48 with the support beams 52 of the patient support system 46 (block 158). For example, as illustrated in FIG. 1, the patient bed 54, having the patient 22 positioned over the patient support 48, may be placed adjacent to the gantry 12 of the medical imaging system 10 such that the patient 22 may be positioned between the support beams 22 of the patient support system 46. Additionally, the patient bed Once the patient support 48 and the patient 22 are properly aligned with the support beams 52 of the patient support system 46, the method 150 includes securing the patient support 48 to the support beams 52 and vertically positioning the patient 22 (block 160). For example, as discussed above, the restraint 64 of the patient support 48 includes the plurality of fasteners 68 that may be used to secure the restraint 64 to the support beams 52. Once secured to the support beams 52, the patient support 48 adopts the hammock-like configuration and secures the patient 22 within the patient support 48, as illustrated in FIG. 3. The patient support system 46 may move vertically to adjust a vertical position of the patient 22 such that the patient 22 is aligned with the bore 50 of the medical imaging system 10.

In certain embodiments, the patient support system 46 may include certain features that may secure equipment associated with the patient 22. For example, the patient support system 46 may include hooks, fasteners, or other features that may be used to attach and secure ECG leads, IV lines, and other items that may be attached to the patient 22. Additionally, the patient support system 46 may include a handle or arm restraint that the patient 22 may hold on to during the imagine procedure, for example, in imaging procedures where the patient 22 is asked to keep their hands over their head.

The method 150 also includes suspending the patient 22 in the patient support 48 (block 164), and positioning the patient 22 within the bore 50 of the medical imaging system 10 for medical imaging and prescribe scan range (block 168). For example, once the patient support 48 is secured to the support beams 52, the height of the patient bed 54 may be adjusted such the patient bed 54 is moved away from the patient support 48 and the patient 22 in the radial direction 82, or the patient bed 54 may be removed from underneath the patient support 48, to suspend the patient 22 in the patient support 48 similar to a hammock. The patient support 48 may be translocated using the translocation system 53 and the support beams 52 to position the patient 22 within the bore 50 of the medical imaging system 10, as shown in FIG. 5.

The method 150 also includes acquiring a scan to image the patient 22 (block 169). As discussed above, the decreased cross-sectional area of the backing 60 and support beams 52 may mitigate attenuation of the radiation (e.g., the beam of X-rays 16) and decrease noise levels that are generally associated with cantilevered patient support systems used in certain medical imaging systems. Accordingly, the image generated from the acquired scans of the patient 22 may be of higher quality compared to images generated from acquired scans where the patient is on a cantilevered patient support. Additionally, due, in part, to the decreased attenuation of the radiation used to acquire the scans, the radiation dose efficiency may be improved compared to cantilevered patient support configurations.

Following imaging of the patient 22 in the medical imaging system 10, the method 150 includes removing the patient 22 from the bore 50 of the medical imaging system 10 and detaching the patient support 48 from the support beams 52 (block 170). For example, once the medical imaging is complete, the translocation system 53 may be used to move the patient 22 and the patient support 48 out of the bore 50 and align the patient 22 over the patient bed 54. The height of the patient bed 54 may be adjusted to raise the patient surface 56 until the backing 60 of the patient support 48 abuts the patient surface 56 of the patient bed 54. Once the backing 60 of the patient support 48 is properly loaded and positioned on the patient surface 56 of the patient bed 54, the operator of the medical imaging system 10 may unfasten the plurality of fasteners 68 to detach the restraint 64 of the patient support 48 from the support beams 52. The patient 22 may be transported to a remote location (e.g., patient room or other area of the clinic or hospital setting) using the patient bed 54. The patient support 48 may be removed at any time after medical imaging has been completed (e.g., before or after the patient 22 is transported to the remote location).

Technical effects of the invention include a patient support system having a hammock-like configuration that includes a backing having a cross-sectional area that is less compared to a cross-sectional area of a patient table used to support patients in cantilevered patient support systems corresponding to certain medical imaging systems. Accordingly, the patient support system disclosed herein may mitigate undesirable attenuation of radiation and noise levels generally associated with cantilevered patient support systems, which generally have a large cross-sectional area. In addition, the hammock-like configuration of the patient support may allow flexibility for positioning patients during medical imaging. For example, the patient may be tilted and/or positioned on their lateral sides. Moreover, the patient support system disclosed herein includes features that facilitate patient transport to and from the medical imaging system. For example, the patient support may be removably coupled to a translocation system associated with the medical imaging system that is used to move the patient into and out of the medical imaging system. In this way, the patient may be positioned on the patient support at a location that is remote from the medical imaging system, and patient and medical staff safety may be increased compared to current patient transfer methods for certain medical imaging procedures, which may include lifting the patient from the patient bed to the patient table of the cantilevered patient support system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A patient support system comprising:
  a support beam configured to translocate along an axial axis of a medical imaging system, wherein at least a portion of the support beam is configured to be disposed within a central bore of the medical imaging system;
  a patient support removably coupled to the support beam and comprising:
    a backing disposed below the support beam and configured to support a patient during an imaging procedure, and
    a restraint extending a longitudinal length of the backing, wherein the restraint comprises a first end coupled to the backing and a second end configured to be removably coupled to the support beam, and wherein the restraint is configured to secure the patient support to the support beam and to restrain the patient within the patient support; and a translocation system comprising a track extending along the axial axis of the medical imaging system and positioned parallel to the support beam, wherein the translocation system is configured to linearly move the support beam in a first direction to position the patient support and the patient within the central bore of the medical imaging system and to move the support beam in a second direction substantially opposite the first direction to move the patient support and the patient out of the central bore of the medical imaging system.

2. The patient support system of claim 1, wherein the restraint comprises a fabric configured to partially surrounds the patient.

3. The patient support system of claim 1, wherein the translocation system comprises extensions disposed between the track and the support beam and radially extending away from the track, wherein the extensions are configured to secure the support beam to the track.

4. The patient support system of claim 3, wherein the support beam is configured to move relative to the extensions to move the support beam in the first direction or the second direction.

5. The patient support system of claim 1, wherein the restraint comprises a plurality of fasteners configured to secure the patient support to the support beam, and wherein the plurality of fasteners are disposed on the second end of the restraint.

6. The patient support system of claim 1, wherein the backing, the support beams, and the restraint are configured to attenuate between approximately 0% and approximately 10% of radiation emitted by a radiation source of the medical imaging system during the imaging procedure.

7. The patient support system of claim 1, wherein the patient support is suspended from the support beam.

8. The patient support system of claim 1, wherein the restraint is oriented orthogonal to the backing when the patient support is secured to the support beam.

9. A medical imaging system, comprising:
a patient support system comprising:
a support beam configured to translocate along an axial axis of the medical imaging system, wherein at least a portion of the support beam is configured to be disposed within a central bore of the medical imaging system;
a patient support removably coupled to the support beam and comprising:
a backing disposed below the support beam and configured to support a patient during an imaging procedure, and
a restraint extending a longitudinal length of the backing, wherein the restraint comprises a first end coupled to the backing and a second end configured to be removably coupled to the support beam, and wherein the restraint is configured to secure the patient support to the support beam and to restrain the patient within the patient support, and wherein the patient support is configured to support the patient as the support beam translocates to position the patient within the central bore of the medical imaging system; and a translocation system positioned parallel to the support beam and configured to linearly move the support beam in a first direction to move the patient support and the patient into the central bore of the medical imaging system and to move the support beam in a second direction opposite the first direction to move the patient support and the patient out of the central bore of the medical imaging system.

10. The medical imaging system of claim 9, wherein the restraint is oriented orthogonal to the backing when the patient support is secured to the support beam, and wherein the patient support is positioned below the support beam.

11. The medical imaging system of claim 9, wherein the backing, the support beams, and the restraint are configured to attenuate between approximately 0% and approximately 10% of radiation emitted by a radiation source of the medical imaging system during the imaging procedure.

12. The medical imaging system of claim 9, wherein a portion of the translocation system is coupled to the medical imaging system.

13. The medical imaging system of claim 9, wherein the translocation system comprises a plurality of radial extensions configured to couple the support beam to the translocation system and to suspend the patient support during the imaging procedure.

14. The medical imaging system of claim 9, wherein the restraint comprises fasteners on the second end, and wherein the fasteners are configured to removably couple the patient support to the support beam during the imaging procedure.

15. The medical imaging system of claim 9, comprising a computed tomography scanner or a positron emission tomography scanner, or both.

16. A method, comprising:
coupling a patient support to a support beam of a patient support system of a medical imaging system, wherein the patient support comprises a backing disposed below the support beam and configured to support a patient during an imaging procedure and a restraint extending a longitudinal length of the backing, wherein the restraint comprises a first end coupled to the backing and a second end configured to removably couple the patient support to the support beam such that the restraint is oriented orthogonal to the backing, and wherein the restraint is configured to secure the patient support to the support beam and to restrain the patient within the patient support; and moving the support beam in a first direction while the patient is supported by the patient support to position the patient support and the patient within a central bore of the medical imaging system using a translocation system coupled to the support beam.

17. The method of claim 16, comprising suspending the patient in the patient support after the restraint is coupled to the support beam and before moving the support beam in the first direction.

18. The method of claim 16, comprising moving the support beam in a second direction opposite the first direction to move the patient support and the patient away from the central bore of the medical imaging system.

* * * * *